United States Patent [19]
Flaherty

[11] Patent Number: 5,954,058
[45] Date of Patent: Sep. 21, 1999

[54] POWER SUPPLY FOR IMPLANTABLE DEVICE

[75] Inventor: Christopher J. Flaherty, Topsfield, Mass.

[73] Assignee: Strato/Infusaid, Inc., Norwood, Mass.

[21] Appl. No.: 08/821,602

[22] Filed: Mar. 20, 1997

Related U.S. Application Data

[63] Continuation of application No. 08/523,083, Sep. 1, 1995.

[51] Int. Cl.$^6$ .................................................. A61M 37/00
[52] U.S. Cl. .......................................... 128/899; 604/131
[58] Field of Search .............................. 607/34; 128/899, 128/DIG. 12; 604/891.1, 114, 131, 132, 141, 156, 70

[56] References Cited

U.S. PATENT DOCUMENTS

| | | | |
|---|---|---|---|
| 3,731,669 | 5/1973 | Fitzgerald | 128/899 |
| 3,774,243 | 11/1973 | Ng et al. | 607/35 |
| 3,826,265 | 7/1974 | Giori et al. | 607/35 |
| 4,294,891 | 10/1981 | Yao et al. | 607/35 |
| 5,431,694 | 7/1995 | Snaper et al. | 607/35 |

*Primary Examiner*—William E. Kamm
*Assistant Examiner*—George R. Evanisko
*Attorney, Agent, or Firm*—Lappin & Kusmer LLP

[57] ABSTRACT

The invention provides an implantable apparatus which includes a power supply capable of converting non-electrical energy such as mechanical, chemical, thermal, or nuclear energy into electrical energy. The invention also provides a method of supplying energy to an electrical device within a mammalian body in which the mammal is implanted with an apparatus including a power supply capable of converting non-electrical energy into electrical energy, and non-electrical energy is transcutaneously applied to the apparatus.

3 Claims, 4 Drawing Sheets

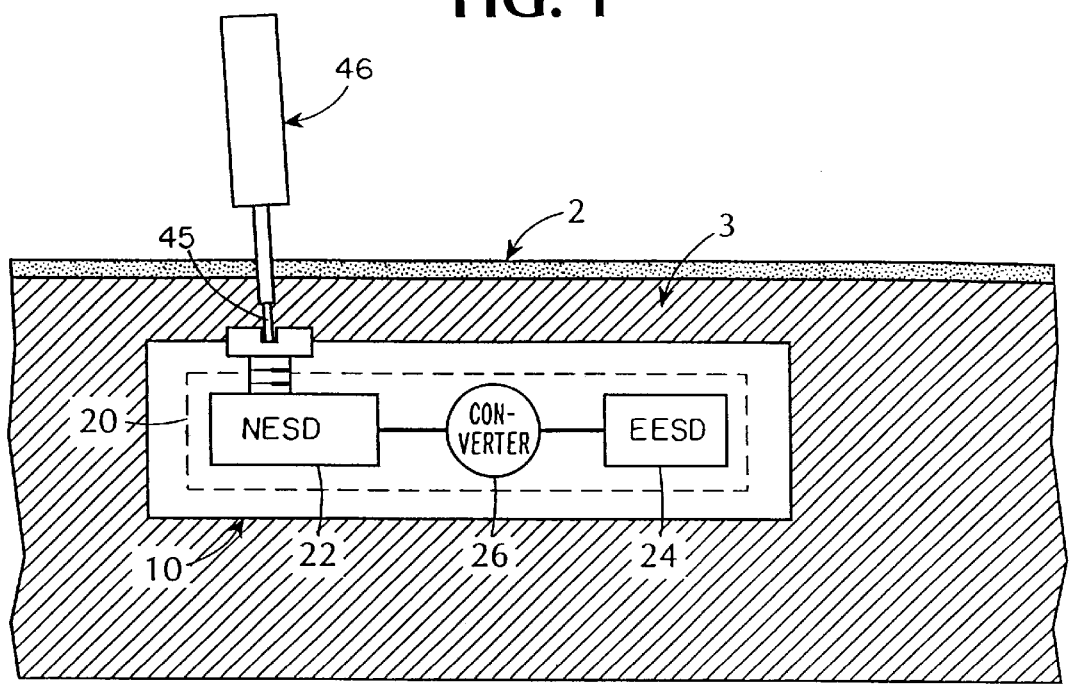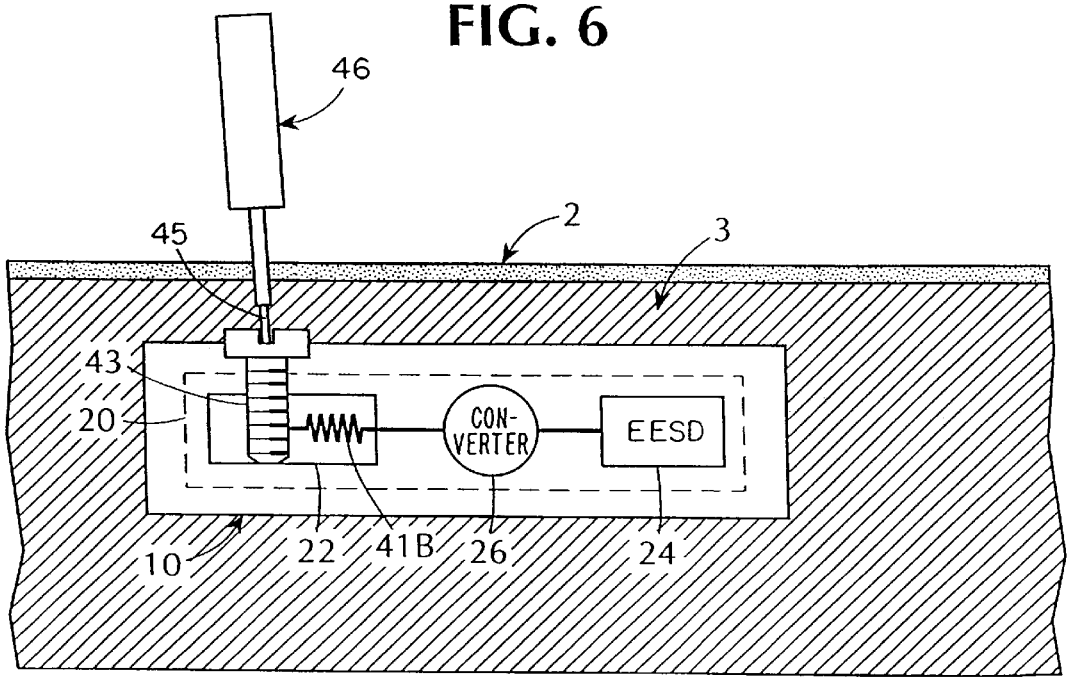

POWER SUPPLY FOR IMPLANTABLE DEVICE

This is a continuation of copending application Ser. No. 08/523,083 filed on Sep. 1, 1995.

The present invention relates to the field of electrically powered devices which are implanted into living bodies for medical purposes. More specifically, the invention relates to novel means for supplying power to such devices.

BACKGROUND OF THE INVENTION

Modern medical science employs numerous electrically powered devices which are implanted in a living body. For example, such devices may be employed to deliver medications, to support blood circulation as in a cardiac pacemaker or artificial heart, and the like. Many implantable devices contain batteries which may be rechargeable by transcutaneous induction of electromagnetic fields in implanted coils connected to the batteries. Transcutaneous inductive recharging of batteries in implanted devices is disclosed for example in U.S. Pat. No. 3,923,060; U.S. Pat. No. 4,082,097; U.S. Pat. No. 4,143,661; U.S. Pat. No. 4,665,896; U.S. Pat. No. 5,279,292; U.S. Pat. No. 5,314,453; U.S. Pat. No. 5,372,605, and many others.

Other methods for recharging implanted batteries have also been attempted. For example, U.S. Pat. No. 4,432,363 discloses use of light or heat to power a solar battery within an implanted device. U.S. Pat. No. 4,661,107 discloses recharging of a pacemaker battery using mechanical energy created by motion of an implanted heart valve.

A number of implanted devices have been powered without batteries. U.S. Pat. No. 3,486,506 and U.S. Pat. No. 3,554,199 disclose generation of electric pulses in an implanted device by movement of a rotor in response to the patient's heartbeat. U.S. Pat. No. 3,563,245 discloses a miniaturized power supply unit which employs mechanical energy of heart muscle contractions to generate electrical energy for a pacemaker. U.S. Pat. No. 3,456,134 discloses a piezoelectric converter for electronic implants in which a piezoelectric crystal is in the form of a weighted cantilever beam capable of responding to body movement to generate electric pulses. U.S. Pat. No. 3,659,615 also discloses a piezoelectric converter which reacts to muscular movement in the area of implantation. U.S. Pat. No. 4,453,537 discloses a pressure actuated artificial heart powered by a second implanted device attached to a body muscle which in turn is stimulated by an electric signal generated by a pacemaker.

In spite of all these efforts, a need remains for efficient generation of energy to supply electrically powered implanted devices.

SUMMARY OF THE INVENTION

The present invention provides an electrically powered implantable apparatus which may be recharged with non-electrical energy. The apparatus of the invention comprises a power supply including a transcutaneously rechargeable non-electrical energy storage device (NESD); an electrical energy storage device (EESD); and an energy converter coupling the NESD and the EESD. The converter includes means for converting non-electrical energy stored in the NESD to electrical energy and for transferring the electrical energy to the EESD, thereby storing the electrical energy in the EESD.

In another embodiment, the invention provides a method of supplying energy to an electrical device within a mammalian body. That method comprises implanting into the mammal an apparatus including a power supply having: a transcutaneously rechargeable NESD; an EESD; and an energy converter coupling the NESD and the EESD. The converter includes means for converting non-electrical energy stored in the NESD to electrical energy and for transferring that electrical energy to the EESD, thereby storing the electrical energy in the EESD. Following implantation, non-electrical energy is applied transcutaneously to said NESD.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 1 shows a schematic diagram of an exemplary implantable apparatus of the invention.

FIG. 6 shows a schematic diagram of an embodiment of the implantable apparatus of the invention which employs a compressible spring for recharging the NESD.

DETAILED DESCRIPTION OF THE INVENTION

Figure 2A:
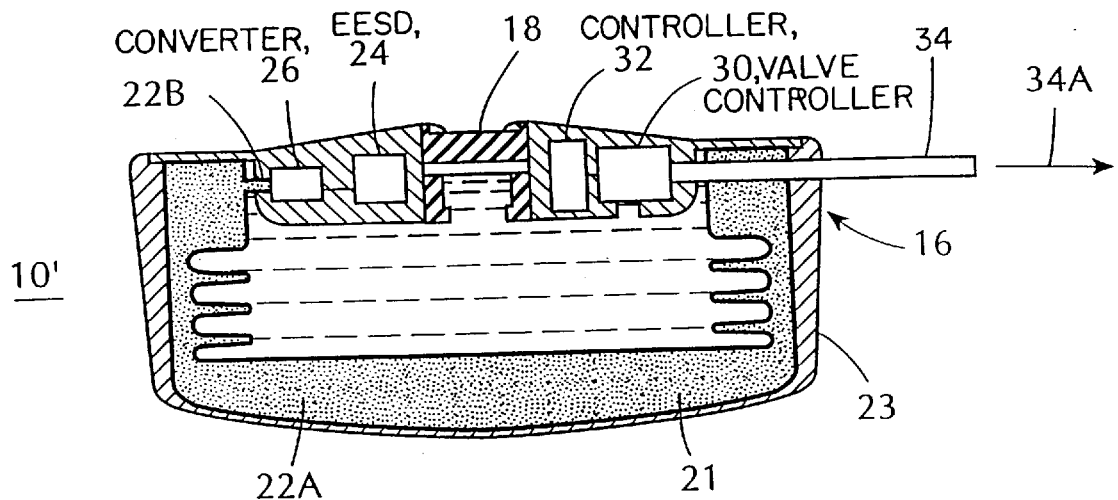
FIG. 2A shows a schematic diagram, in section, of an embodiment of the implantable apparatus of the invention which employs a closed fluid system for recharging the NESD.

The invention as depicted in FIG. 1 includes an apparatus 10 implanted under skin 2 and disposed within subcutaneous tissue 3. Apparatus 10 includes a power supply 20 which contains a transcutaneously rechargeable non-electrical energy storage device (NESD) 22; an electrical energy storage device (EESD) 24; and an energy converter 26 coupling NESD 22 and EESD 24. Energy converter 26 includes means for converting non-electrical energy stored in NESD 22 to electrical energy and for transferring electrical energy to EESD 24, thereby storing the electrical energy in EESD 24.

Any device may be used to store non-electrical energy in accordance with the invention. Many such devices are known which are suitable to act as NESD 22. For example, devices capable of storing mechanical energy, physical phase transition/pressure energy, chemical energy, thermal energy, nuclear energy, and the like, may be used in accordance with the invention. Similarly, any device may be used to store electrical energy in accordance with the invention and to act as EESD 24. Suitable EESDs include, for example, rechargeable batteries and capacitors. Any device capable of converting non-electrical energy to electrical energy may be used to convert energy in accordance with the invention and to act as energy converter 26. When the non-electrical energy used is mechanical energy, for example, energy converter 26 may include a piezoelectric crystal and associated rectifier circuitry as needed. The apparatus of the invention may also include an implanted electrical circuit, such as a driver for a solenoid driven valve, and means for extracting electrical energy from EESD 24 and applying the extracted electrical energy to the electrical circuit.

Figure 2B:
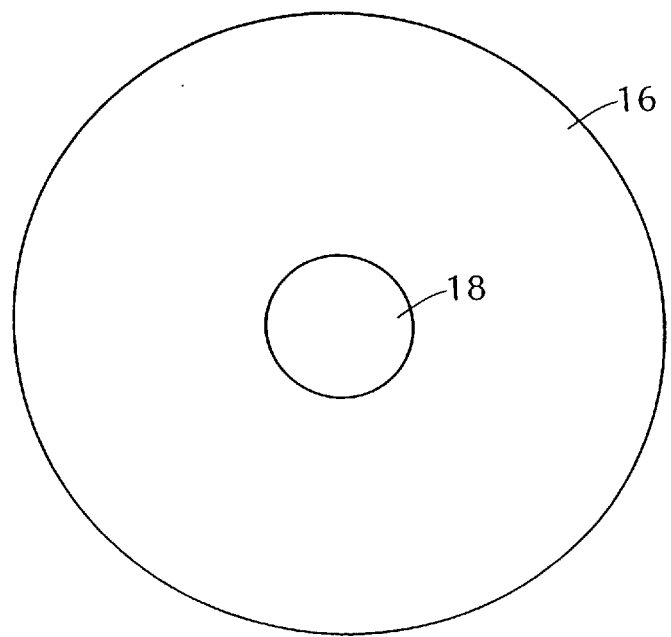
FIG. 2B shows a top plan view of the embodiment of FIG. 2A.
Figure 3:
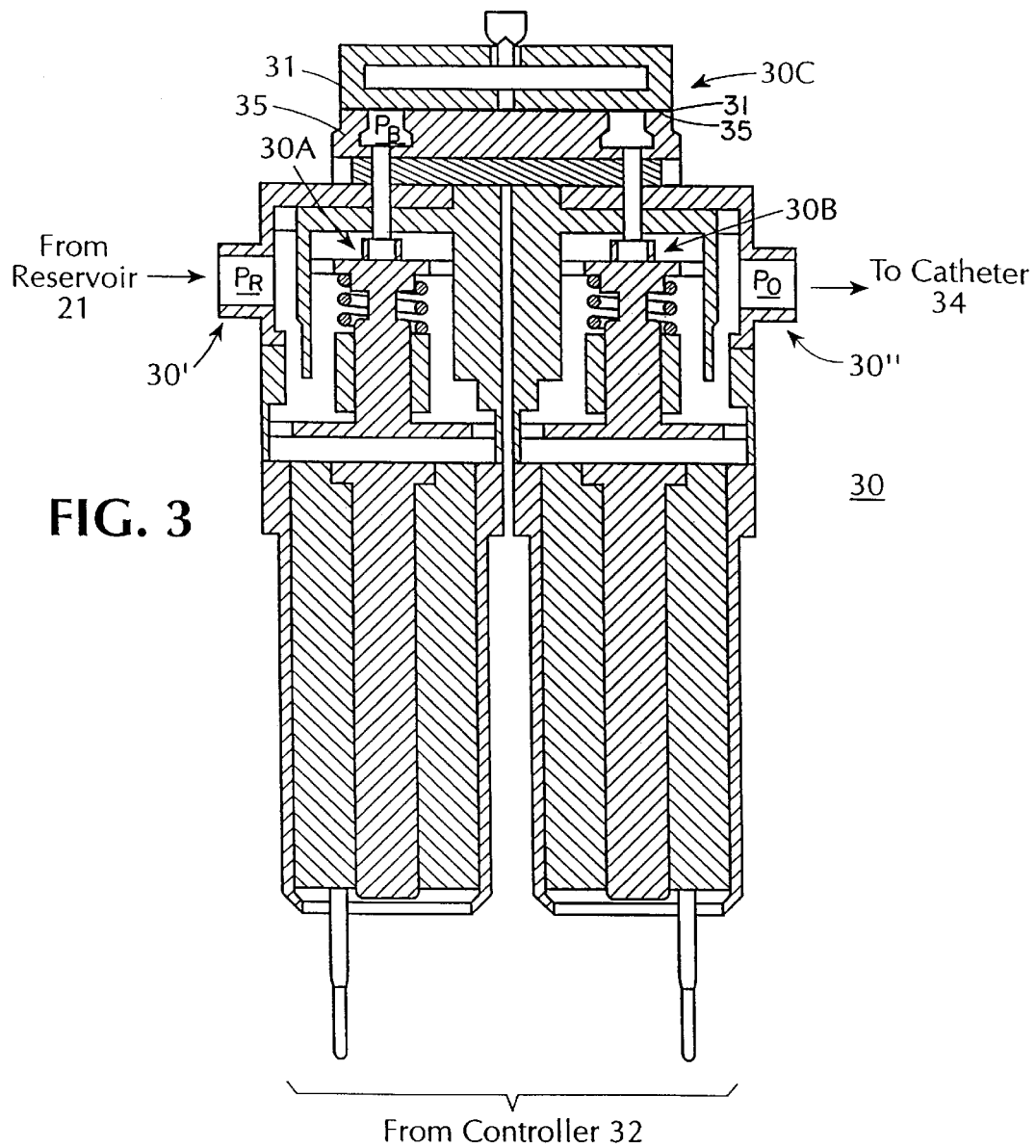
FIG. 3 shows a sectional view of the valve/accumulator assembly of the embodiment of FIG. 2A.

When the non-electrical energy is mechanical energy, for example, NESD 22 may include a closed fluid system wherein recharging occurs by compression of the fluid. Such a system 10' is represented in FIGS. 2A and 2B. System 10' is an implantable medicant infusion pump which includes a biocompatable housing 16 for example, made of titanium, having a piercable septum 18 centrally located in its top surface. A bellows assembly 23 extends from the septum 18 to define a variable volume fluid (or medicant) reservoir 21. A valve/accumulator assembly 30 is coupled between reservoir 21 and an exit catheter 34 to establish a selectively controlled fluid/medicant flow path 34A from the reservoir 21 to a point within the body at the distal tip of catheter 34. In one form of the invention, the valve/accumulator assembly 30 has the form shown in FIG. 3, and includes two solenoid valves 30A, 30B which control the filling and emptying of an accumulator 30C in response signals applied by a controller 32. In response to such signals, the accumulator of assembly 30 drives a succession of substantially uniform pulses of medicant through said catheter 34.

In the illustrated embodiment, valve/accumulator 30, includes an input port 30' coupled between reservoir 21 and valve 30A and an output port 30" coupled between valve 30B and catheter 34. The accumulator includes a diaphragm 31 that is movable between limit surface 33 one side of the diaphragm and limit surface 35 on the other side of the diaphragm. Surface 35 includes open-faced channels therein, defining a nominal accumulator volume that is coupled to valves 30A and 30B. A pressure $P_B$ is maintained on the side of diaphragm 31 that is adjacent to surface 35. A pressure of $P_R$ is maintained at port 30', due to the positive pressure exerted on bellows 23 from the fluid in chamber 22A, as described more fully below. A pressure $P_O$ is at port 30", reflecting the relatively low pressure within the patient at the distal end of catheter 34. In operation, the pressure $P_B$ is maintained between the $P_R$ and $P_O$. Normally, valves 30A and 30B are closed, and diaphragm 31 is biased against surface 33. To generate an output pulse of medicant in catheter 34, valve 30A is opened, and the pressure differential between port 30' and $P_B$ drives fluid into the accumulator 30, displacing the diaphragm 31 to surface 35. The valve 30A is then closed and valve 30B is opened. In response, the pressure differential $P_B-P_O$ drives an increment of fluid (substantially equal to the previously added fluid) into catheter 34, displacing the diaphragm back to surface 33. Valve 30B then closes, completing the infusion cycle. All valve operations are under the control of controller 32. In other embodiments, other medicant infusion configurations may be used.

The controller 32 includes microprocessor-based electronics which may be programmed, for example, by an external handheld unit, using pulse position modulated signals magnetically coupled to telemetry coils within housing 16. Preferably, communication data integrity is maintained by redundant transmissions, data echo and checksums.

In one form of the invention, the bellows assembly 23, together with the inner surface of housing 16, define a variable volume closed fluid chamber 22A which contains a predetermined amount of a gas phase fluid, such as air. The charge of fluid in chamber 22A maintains a positive pressure in the reservoir 21, so that with appropriately timed openings and closings of the valves 30A and 30B, infusate from reservoir 21 is driven through catheter 34. A port 22B couples the chamber 22A to a mechanical-to-electrical energy converter 26, which in turn is coupled to a rechargeable storage battery 24. The battery 24 is coupled to supply power to controller 32 and valves 30A and 30B, and may be used to power other electronic circuitry as desired.

Figure 4:
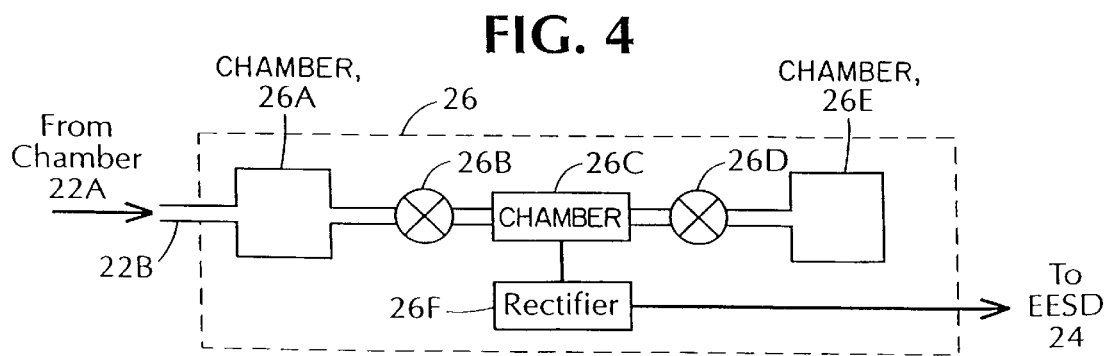
FIG. 4 shows a schematic representation of the mechanical-to-electrical energy converter of the embodiment of FIG. 2A.

An exemplary mechanical-to-electrical energy converter 26 is shown in FIG. 4. That converter 26 includes a first chamber 26A which is coupled directly via port 22B to chamber 22A, and is coupled via valve 26B, energy extraction chamber 26C, and valve 26D to a second chamber 26E. Energy extraction chamber 26C is preferably a tube having a vaned flow restrictors in its interior, where those flow restrictors are made of piezoelectric devices. A rectifier network 26F is coupled to the piezoelectric devices of chamber 26C and provides an electrical signal via line 26' to EESD 24. The valves 26B and 26D are operated together in response to control signals from controller 32. When those valves are open, fluid (in gas phase) flows from chamber 22A via chamber 26A and 26C to chamber 26E when the pressure in chamber 22A is greater than the pressure in chamber 26E, and in the opposite direction when the pressure in chamber 22A is less than the pressure in chamber 26E. In both flow directions, the vanes of chamber 26C are deflected by the flowing fluid, which results in generation of an a.c. electrical potential, which in turn is rectified by network 26F to form a d.c. signal used to store charge in EESD 24.

In the operation of this form of the invention, with valves 26B and 26D closed, the chamber 22A is initially charged with fluid, such as air, so that the fluid in chamber 22A exists in gas phase at body temperature over the full range of volume of reservoir 21. Initially, bellows assembly 23 is fully charged with medicant, and thus is fully expanded to maximize the volume of the reservoir 21. The device 10' is then implanted. After implantation of the device 10', and valves 26B and 26D are opened, thereby resulting in gas flow through chamber 26C until equilibrium is reached. Then valves 26B and 26D are closed. Thereafter, in response to its internal programming, the controller 32 selectively drives valve/accumulator 30 to complete a flow path between reservoir 21 and cannula, and as described above in conjunction with FIG. 3, driving medicant from reservoir 21, via cannula 34 (and flow path 34A) to a point within the body at a desired rate. In response to that transfer of medicant from reservoir 21, the volume of reservoir 21 decreases, causing an increase in the volume of chamber 22A. As the latter volume increases, a low pressure tends to be established at port 22B. That pressure, with valves 26B and 26D open, in turn draws gas from chamber 26E and through chamber 26C, thereby generating an electrical signal at rectifier 26F. When the reservoir 21 is depleted of medicant, a device such as a syringe may be used to pierce the skin and penetrate the septum 18, and inject a liquid phase medicant or other infusate into reservoir 21, thereby replenishing the medicant in reservoir 21. As liquid is injected into reservoir 21, the bellows assembly 23, expands causing an increase in the volume of reservoir 21 and a decrease in the volume of the phase fluid in chamber 22A, representing storage of mechanical energy. Valves 26B and 26D are then opened, establishing an equilibrating gas flow through chamber 26C, resulting in transfer of charge to EESD 24. In this embodiment, valves 26B and 26D are on opposite sides of chamber 26C. In other embodiments, only one of these valves may be present, and the converter 26 will still function in a similar manner. In yet another embodiment, where chamber 26C has a relatively high flow impedance, there is no need for either of valves 26B and 26D.

In another form, the bellows assembly 23, together with the inner surface of housing 16, define a variable volume closed fluid chamber 22A which contains a predetermined amount of a fluid, such as freon, which at normal body temperatures exists both in liquid phase and gas phase over the range of volume of chamber 22A. Preferably, the fluid in reservoir 22A is R-11 Freon, which at body temperature 98.6° F. and in a two phase closed system, is characterized by a vapor pressure of approximately 8 psi, where the ratio of liquid-to-gas ratio varies with the volume of chamber 22A. The charge of fluid in chamber 22A maintains a positive pressure in the reservoir 21, so that with appropriately timed openings and closings of the valves 30A and 30B, infusate from reservoir 21 is driven through catheter 34. A port 22B couples the chamber 22A to a mechanical-to-electrical energy converter 26, which in turn is coupled to a rechargeable storage battery 24. The battery 24 is coupled to supply power to controller 32 and valve 30A and 30B. The mechanical-to-electrical energy converter 26 is the same as that described above and as shown in FIG. 4. In this form of the invention, the non-electrical energy is referred to as physical phase transition/pressure energy.

In the operation of this form of the invention, the chamber 22A is initially charged with fluid, such as Freon R-11, so that the fluid in chamber 22A exists in both liquid phase and gas phase at body temperature over the full range of volume of reservoir 21. Initially, bellows assembly 23 is fully charged with medicant and thus fully expanded to maximize the volume of reservoir 21. The device is then implanted. Then after implantation of the device 10', in response to its internal programming, the controller 32 selectively drives valve/accumulator 30 to complete a flow path between reservoir 21 and cannula, and as described above, in conjunction with FIG. 3, to drive medicant from reservoir 21, via cannula 34 (and flow path 34A) to a point within the body at a desired rate. In response to that transfer of medicant from reservoir 21, the volume of reservoir 21 decreases, causing an increase in the volume of chamber 22A. As the latter volume increases, a low pressure tends to be established at port 22B prior to achievement of equilibrium. That pressure, with valves 26B and 26D open, in turn draws gas from chamber 26E and through chamber 26C, thereby generating an electrical signal at rectifier 26F. As the reservoir 21 is depleted of medicant, a device such as a syringe may be used to pierce the skin and penetrate the septum 18, followed by injection of a liquid phase medicant or other infusate into reservoir 21, thereby replenishing the medicant in reservoir 21. As liquid is injected into reservoir 21, the bellows assembly expands causing an increase in the volume of reservoir 21 and a decrease in the volume of the two phase fluid in chamber 22A. That results in an increase in pressure at port 22B representing storage of mechanical energy. Valves 26B and 26D are then opened, establishing an equilibrating gas flow through chamber 26C, resulting in storage of charge in EESD 24. As the bellows assembly 23 is expanded, the re-compression of chamber 22A effects a re-charge of battery 24. The rectifier 26F establishes charging of battery 24 in response to forward and reverse gas flow caused by the expansion and contraction of bellows assembly 23. The present embodiment is particularly useful in configurations similar to that in FIG. 2A, but where the various components are positioned within housing 16 so that the converter 26 normally is higher than the liquid-gas interface in chamber 22A. When implanted, and where the user is upright. With that configuration, and appropriately charged with Freon, the fluid within converter 26 is substantially all in gas phase. In order to prevent liquid phase Freon from passing to chamber 26C when the user is prone, a gravity activated cut-off valve (not shown) may be located in port 22B.

Selectively operable infusion pumps are known, and their use and operation is described in detail in U.S. Pat. No. 3,951,147; U.S. Pat. No. 4,258,711; and U.S. Pat. No. 4,496,343. Such pumps are commercially available, for example, the Model 400 available from Strato/Infusaid, Inc., Norwood, Mass. USA.

Figure 5A:
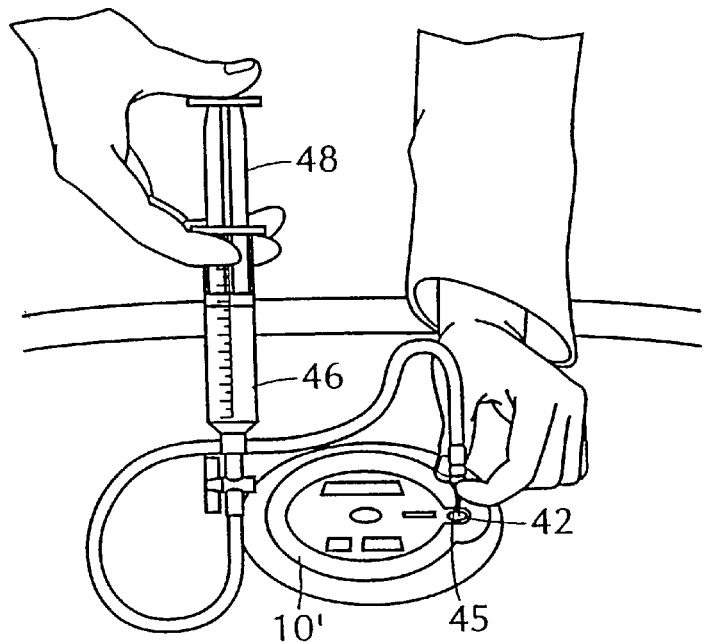
FIG. 5A shows the first step of recharging the embodiment of FIG. 2A.
Figure 5B:
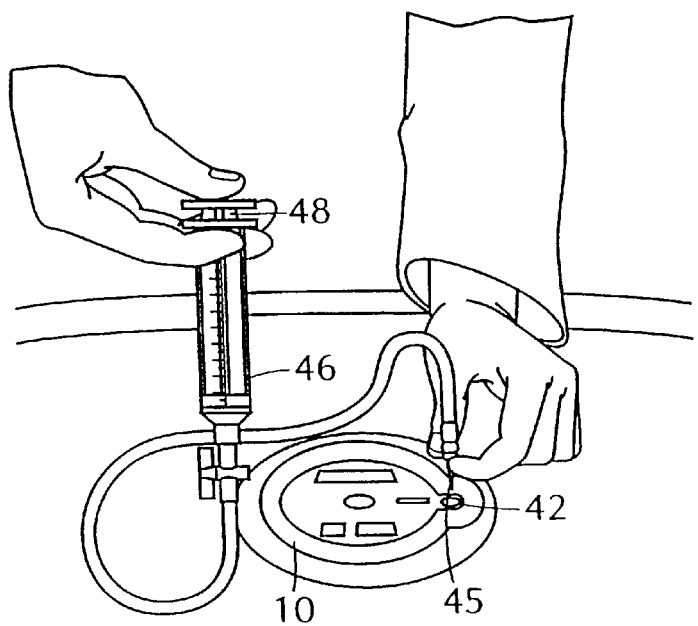
FIG. 5B shows the second step of recharging the embodiment of FIG. 2A.

FIGS. 5A and 5B depict operation of the infusion pump embodiment, in which a cannula 45 is inserted through the septum 18 to the reservoir 21. Cannula 45 is in fluid connection with syringe 46, which contains the medication to be injected into medication reservoir 21. In the first recharging step shown in FIG. 5A, plunger 48 of syringe 46 is in a retracted position as the result of the presence of the medication within syringe 46. In the second recharging step shown in FIG. 5B, plunger 48 is inserted into syringe 46 as the result of injection of the medication via cannula 45 through septum 18, and into reservoir 21.

In another embodiment in which mechanical energy is stored in NESD 22, shown in FIG. 6, NESD 22 includes a compressible spring 41B. Spring 41B is connected to a compressor assembly 43 which may be accessed transcutaneously. Any means may be used to compress spring 41B. As shown in FIG. 6, compressor 43 includes a screw which may be turned by application of a laparoscopic screwdriver 45.

When the non-electrical energy stored in NESD 22 is chemical energy, NESD 22 includes a fluid activatable chemical system. Recharging may occur by injection of one or more chemical solutions into NESD 22. Any chemical solutions may be used to store chemical energy in NESD 22 in accordance with this embodiment of the invention. For example, a solution of electrolytes may be used to store chemical energy in NESD 22.

When the non-electrical energy stored in NESD 22 is thermal energy, NESD 22 includes a thermal differential energy generator capable of generating electrical energy when a fluid having a temperature greater than normal mammalian body temperature is injected into the generator. By way of example, a Peltier effect device may be used, where application of a temperature differential causes generation of an electrical potential. Alternatively, a bimetallic assembly may be used where temperature-induced mechanical motion may be applied to a piezoelectric crystal which in turn generates an electrical potential.

In another embodiment, the invention provides a method of supplying energy to an electrical device within a mammalian body which comprises implanting into the mammal an apparatus including a power supply having: a transcutaneously rechargeable NESD; an EESD; and an energy converter coupling said rechargeable means and the storage device, where the converter converts non-electrical energy stored in the NESD to electrical energy and transfers the electrical energy to the EESD, thereby storing the electrical energy in the EESD; and transcutaneously applying non-electrical energy to the NESD. Any of the devices described above may be used in the method of the invention.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. A rechargeable electrically powered implantable infusion pump and power unit therefor, for intracorporeally dispensing a liquid in a body of a living being, with said infusion pump and power until therefor being capable of subcutaneous implantation in said body of said living being, said infusion pump and power unit comprising:

A. a rigid or semi-rigid outer pump housing;

B. a flexible liquid storage chamber inside said outer-pump housing for containing a liquid to be dispensed intracorporeally in the body of said being by said infusion pump, said liquid storage chamber having a variable volume and a transcutaneously accessible self-sealing inlet and outlet port in communication with said outer-pump housing, such that said liquid can alternatively be introduced into said chamber through said port to refill said chamber, and be pumped out of said chamber through said port upon actuation of electrically powered infusion pump means for intracorporeally dispensing said liquid in the body of said being;

C. electrically powered infusion pump means for causing said liquid to be pumped out of said liquid storage chamber through said port thereof and dispensed within said body of said living being upon actuation of said infusion pump means;

D. a charging fluid storage chamber at least in part surrounding said liquid storage chamber and containing a two phase charging fluid, wherein the liquid phase to gas phase ratio of said charging fluid is representative of a store of potential energy in the form of physical phase transition/pressure energy which is transferrable into kinetic energy upon the physical phase transition of said charging fluid due to the vaporization of said charging fluid form its liquid phase to its vapor phase;

E. rechargeable electrical energy source means contained within said outer-pump housing, for rechargeably receiving and storing electrical energy and for supplying said stored electrical energy to power said infusion pump means; and F. energy converter means in communication with both said charging fluid storage chamber and said rechargeable electrical energy source means, and contained within said outer-pump housing, for converting the released physical phase transition/pressure potential energy of said charging fluid to said electrical energy and for supplying said electrical energy to said rechargeable electrical energy source means.

2. The infusion pump and power unit according to claim 1 wherein said charging fluid is freon.

3. The infusion pump and power unit according to claim 1 wherein said rechargeable electrical energy source means is selected from the group consisting of an electrochemical cell, a battery, and an electrical capacitor.

* * * * *